United States Patent [19]

Katz et al.

[11] Patent Number: 5,769,084
[45] Date of Patent: Jun. 23, 1998

[54] METHOD AND APPARATUS FOR DIAGNOSING SLEEP BREATHING DISORDERS

[75] Inventors: Richard A. Katz, East Lyme, Conn.; Michael S. Lawee, Marblehead; A. Kief Newman, Woburn, both of Mass.

[73] Assignee: The United States of America as represented by the Secretary of the Navy, Washington, D.C.

[21] Appl. No.: 687,098

[22] Filed: Jul. 10, 1996

[51] Int. Cl.$^6$ .................................................. A61B 5/0472
[52] U.S. Cl. .......................................................... 128/700
[58] Field of Search ................................... 128/700, 702, 128/699, 716

[56] References Cited

U.S. PATENT DOCUMENTS 5,201,321  4/1993  Fulton ...................................... 128/702
5,588,425  12/1996  Sackner et al. ......................... 128/700

*Primary Examiner*—Scott M. Getzow
*Attorney, Agent, or Firm*—Michael J. McGowan; Prithvi C. Lall; Michael F. Oglo

[57] ABSTRACT

An apparatus and method for identifying the timing of the onset of and duration of an event characteristic of sleep breathing disorder. Chaotic processing techniques analyze data concerning one or more cardio-respiratory functions such as nasal air flow, chest wall effort, oxygen saturation, heart rate and heart activity. Excursions of the resulting signal beyond a threshold provide markers for the timing of such an event that is useful in the diagnosis of obstructed sleep apnea and other respiratory dysfunctions.

24 Claims, 6 Drawing Sheets d = SAMPLE INTERVAL
p = DELAY T

METHOD AND APPARATUS FOR DIAGNOSING SLEEP BREATHING DISORDERS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION (1) Field of the Invention

This invention is generally related to methods and apparatus for performing medical diagnoses and particularly to a method and apparatus for diagnosing individuals with sleep breathing disorders or other physiological respiratory functions.

(2) Description of the Prior Art

Sleep breathing disorders and other physiological respiratory dysfunctions in humans constitute an area requiring diagnosis. One such area is called obstructive sleep apnea or sleep disorder breathing. Within the pediatric, infant and newborn population the incidence of apparent life threatening events, sudden infant death syndrome and sleep disorder breathing have all been well documented. Sleep apnea also affects over 25% of apparently healthy adults age 55 and older. Sleep apnea contributes to daytime fatigue, increased work place accidents and a number of cardiovascular disorders. The need for a relatively easily implemented procedure exists to provide efficient methods and procedures for diagnosing these various physiological respiratory dysfunctions.

U.S. Pat. No. 4,982,738 to Griebel discloses a diagnostic apnea monitor system that records snoring and respiration sounds made by a patient as well as the patient's heart rate while the patient is sleeping. Signals indicative of snoring sounds and the time intervals therebetween are produced from the recorded respiration. The system generates a first respiration disturbance index representing the number of intervals per hour between episodes of snoring. An average heart rate is also generated in response to the patient's recorded second respiration disturbance index representing the number of episodes per hour in which the patient's heart rate remained at 90% to 109% of its average rate is calculated. A physician then evaluates the first and second disturbance indices to determine whether obstructive sleep apnea is indicated.

U.S. Pat. No. 5,101,831 to Koyama et al. discloses a system for discriminating a sleep state and selectively waking a patient. This system provides variation indices representing the variation of a biological signal on the basis of a first variation amount denoting a tendency of a time series of measured biological signal to increment from the starting time of the measurement and a second variation amount denoting the temporal variation of the biological signal. These signals enable the discrimination of different sleep states, namely the NREM and REM sleep states, on the basis of the distribution of the density of the variation indices exceeding a predetermined threshold.

U.S. Pat. No. 5,105,354 to Nishimura provides a method and apparatus for correlating respiration and heartbeat variability and particularly a method for forecasting sudden infant death syndrome by investigating the correlation between respiration and heart beat in a normal state and a sleep-apnea state of a newborn. In essence the system detects respiratory information, produces an envelope indicative of the respiration information and samples the envelope to produce a fast Fourier transform spectrum of the envelope information. Simultaneously the system detects cardio-electric information in the form of an EKG, detects the peak value and calculates a sequential R—R interval series that is fast Fourier transformed into a spectrum of the R—R interval variation. These two complex conjugations are multiplied and, through a fast Fourier transform, analyzed to calculate a correlation between respiration and heart beat that can then be evaluated to identify the state just before the normal state of a newborn will convert to the state of sleep apnea and forecast sudden death syndrome.

U.S. Pat. No. 5,385,144 to Yamanishi et al. discloses a respiration diagnosis apparatus that distinguishes between obstructive sleep apnea and central apnea automatically. An analog signal processor generates pulse wave signals based on light received from a light emitting means and passing through or reflecting off living tissue. A pulse wave line analog signal processor extracts change components of a base line of the generated pulse wave signal. A master microcomputer distinguishes between obstructive apnea and central apnea on the basis of the extracted pulse wave base line change components.

U.S. Pat. No. 5,398,682 to Lynn discloses a method and apparatus for the diagnosis of sleep apnea utilizing a single interface with a human body part. More specifically, the diagnosis identifies the desaturation and resaturation events in oxygen saturation of a patient's blood. The slope of the events is determined and compared against various information to determine sleep apnea.

It has also been recognized that cardio and respiratory signals are signals of non-linear dynamical systems. U.S. Pat. No. 5,404,298 to Wang et al. and 5,453,940 to Broomhead et al. disclose dynamical system analyzers or chaos analyzers useful in determining characteristics based upon such dynamical system signals. Additional information on the use of chaos is contained in Strogatz, Steven H., Non-linear Dynamics in Chaos, Reading, Mass., Addison Wellsley Publishing Company, 1994, p. 379.

Notwithstanding the existence of the foregoing prior art, the current conventional approach for diagnosing sleep apnea is to admit a patient to a hospital or sleep center for the evening or to transport various diagnostic equipment to a patient's home. Myriad sensors are attached to the patient to measure brain waves, heart rate, blood pressure, respiration, oxygen saturation, chest wall movement, leg movement and other functions. Apparatus monitors these functions through the sleep cycle. Attending personnel annotate the timing of other events as they may occur, including the patient's snoring levels and intervals. All this information is provided in a graphical form to a physician who determines the timing and duration of obstructive sleep apnea episodes and related information. The normal diagnosis modality of choice remains this classical diagnosis of evaluating raw data from a number of monitored functions in light of experience and a priori knowledge in the field.

SUMMARY OF THE INVENTION

Therefore it is an object of this invention to provide a method and apparatus for facilitating the diagnosis of sleep breathing disorders.

Another object of this invention is to provide a method and apparatus for generating markers that identify the onset and duration of an event characteristic of a sleep breathing disorder.

Still another object of this invention is to provide a method and apparatus for facilitating the accumulation of data and processing that data to assist a physician's analysis of sleep breathing disorders.

In accordance with this invention, at least one cardio-respiratory function is monitored over time. A digitized time series representation of each monitored cardio-respiratory function is generated. Chaotic processing of the corresponding time series representation yields a processed signal. Excursions of this signal beyond a corresponding threshold value indicate the time of an onset of an event and its duration.

BRIEF DESCRIPTION OF THE DRAWINGS

The appended claims are intended to point out with particularity and to claim distinctly the subject matter of this invention. The various objects, advantages and novel features of this invention will be more fully apparent from a reading of the following detailed description in conjunction with the accompanying drawings in which like reference numerals refer to like parts, and in which:

DESCRIPTION OF THE PREFERRED EMBODIMENT

Figure 1:
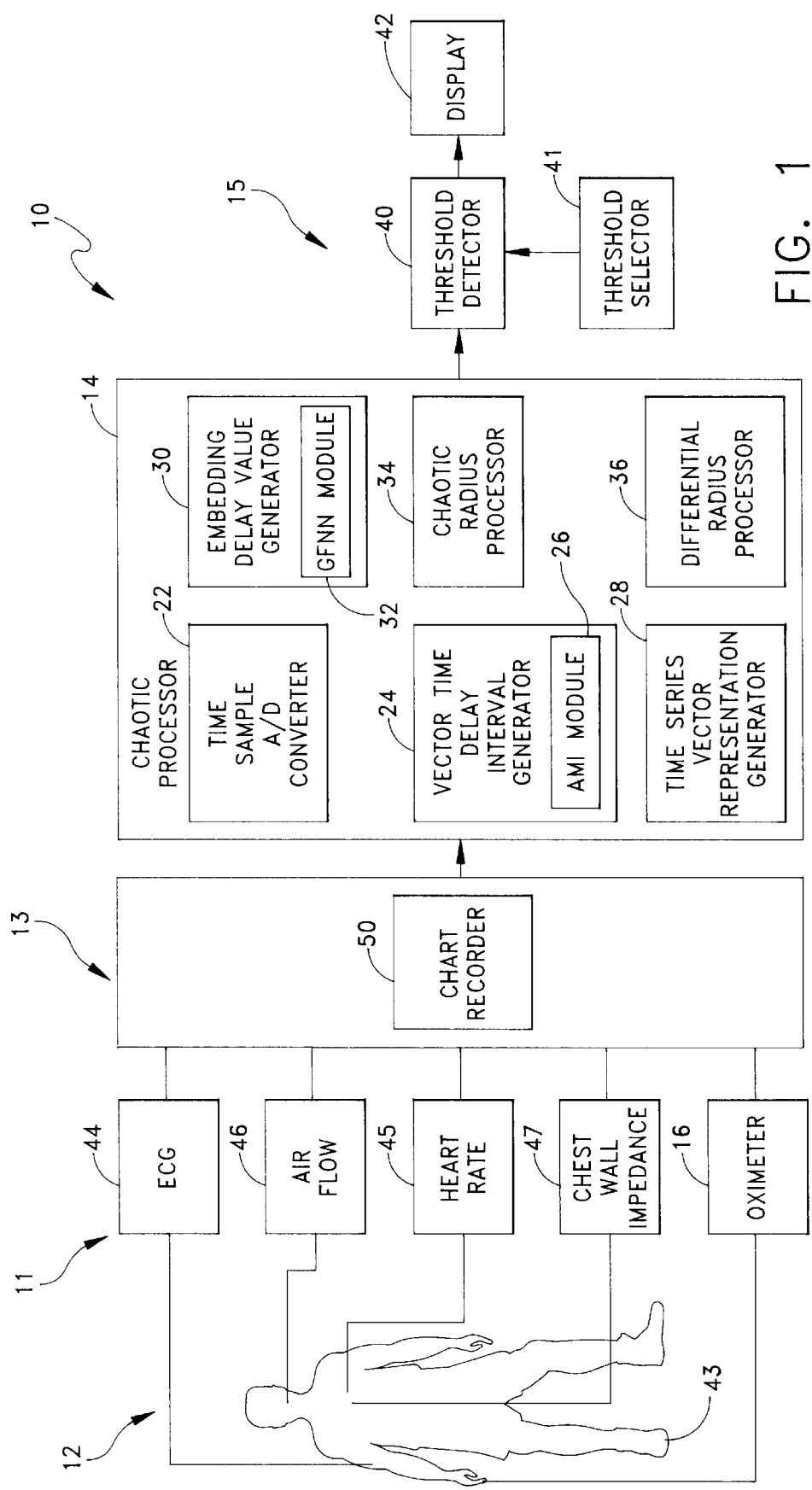
FIG. 1 depicts a patient and, in block diagram form, apparatus for implementing this invention.

Apparatus 10 embodying this invention includes monitors 11 for monitoring at least one cardio-respiratory function of a patient 12 over time. The monitors 11 produce signals that a selector 13 can convey to a chaotic processor 14 that converts each selected signal into a time series representation of the monitored cardio-respiratory function and then generates a signal for that function based upon chaotic processing of the time series representation. An output 15 then identifies as a marker each excursion of the signal beyond a corresponding threshold value thereby to indicate the timing of the onset of an event and its duration.

FIG. 1 discloses specific embodiments of the monitors 11, chaotic processor 14 and output 15. As shown the selector 13 could act as a multiplexer or switch to sample each of these signals in seriatim. It will be apparent that the use of the selector is for purposes of explanation only. If on-line results were required the components of the chaotic processor 14 could be duplicated either by incorporating multiple chaotic processors or by time sharing programs within the single chaotic processor in a manner synchronized by the selection of signals and known in the art.

One of the monitors 11, for example, is an oximeter 16 that, as known, attaches to an individual's index finger and provides an indication of oxygen saturation levels. By way of example and introduction, the output of the oximeter 16 could be a strip chart and the function of the selector could be provided by apparatus that automatically or with manual intervention provides an input to a digital-to-analog converter or otherwise enables the signal to be submitted into the chaotic processor in an analog form. Alternatively the analog signals from the oximeter 16 could be digitized immediately for storage in a local memory.

Figure 2:
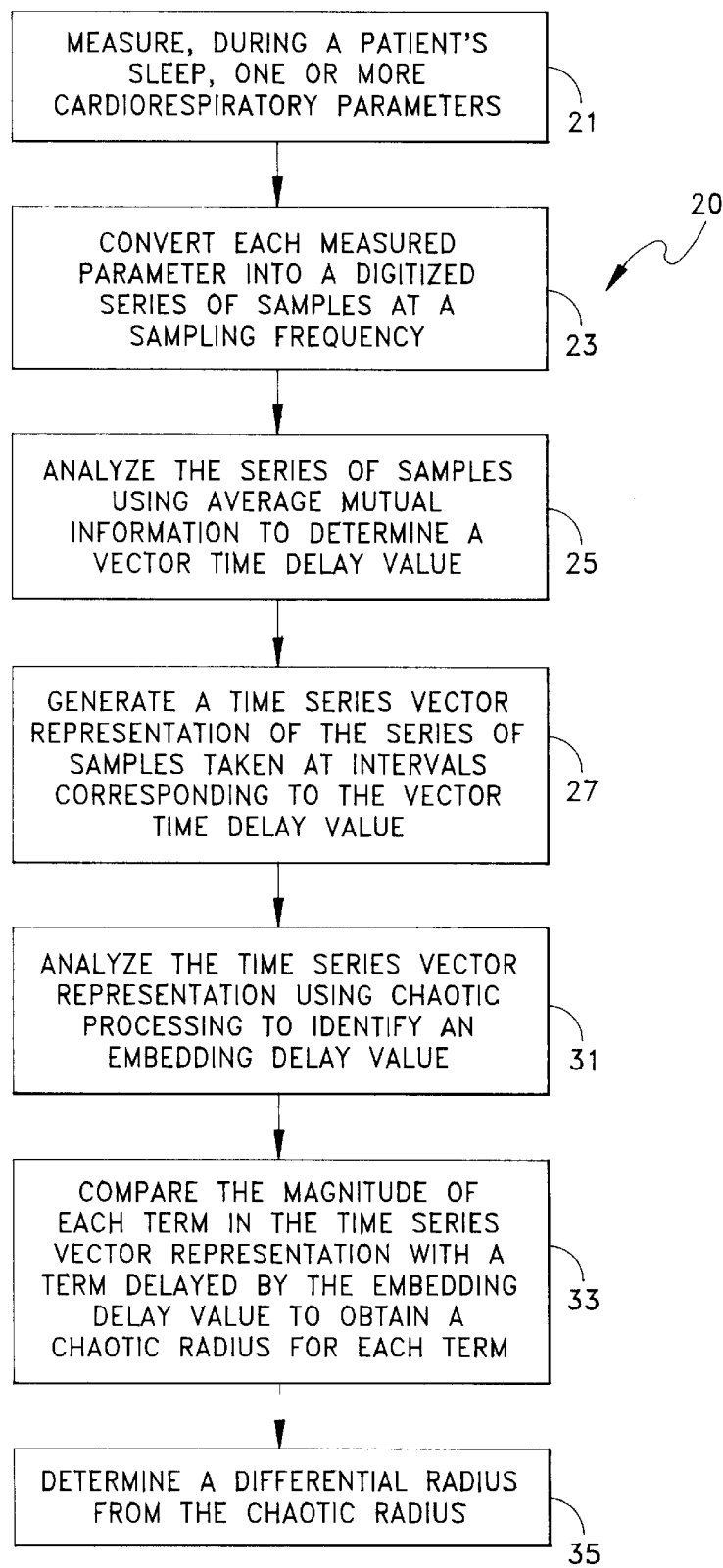
FIG. 2 is a flow chart representing the method in accordance with this invention employed by the apparatus in FIG. 1.

Before discussing each of the monitors 11 and their respective signals it will be helpful to review the operation of the chaotic processor 14. Essentially the chaotic processor converts the analog signal from the selector 13 into either a chaotic radius signal and, for some cardio-respiratory functions, a differential radius signal. FIG. 2 depicts the steps in one method for analyzing such a signal to determine the timing of the onset of an event characteristic of a sleep breathing disorder and its duration. Particularly, as an initial step, the system uses the signal from one of the monitors 11 to measure a cardio-respiratory function such as oxygen saturation. A time sample A/D converter 22 in the chaotic processor 14 converts the measured function into a digitized time series of samples of the monitored function at a sampling frequency.

The sampling frequency must be selected to provide adequate sampling so that the following steps in the process will have sufficient data for providing reliable results with a reasonable temporal resolution. Oversampling is preferable to undersampling although this will increase the burdens of the processing time and complexity. It has been found that the minimum sampling frequency ought to be greater than the greatest frequency of physiologic relevance with respect to the monitored cardio-respiratory function. As a rule of thumb, a sampling frequency of ten times the Nyquist sampling frequency provides good results. Given the time scales involved with the diagnosis of sleep apnea, a sampling frequency of 40 Hz to 100 Hz has been found to be effective and a good compromise between the sampling objectives and burdens that significant oversampling would impose on the system. However, higher sampling frequencies might be used to enable selective time intervals to be analyzed more critically with a shorter sampling interval.

More specifically, the converter 22 in FIG. 1 and step 23 in FIG. 2 produce a digitized representation of the incoming cardio-respiratory function signal in the form of a scalar time series having the general form:

$$v(n)=v(t+ndt) \tag{1}$$

where "t" is the start time for the diagnosis, "dt" is the sample interval (e.g., 0.025 seconds at a 40 Hz sampling frequency) and "n" is the sample number and n=1, 2, 3, . . . N.

A vector time delay interval generator 24 in FIG. 1 processes this scalar time series to determine an interval at which a series of vectors should be generated. This process can use several known techniques. One is a linear auto correlation technique. When the results of the auto correlation technique are plotted, the interval to the first zero crossing can be selected as the vector time delay.

Step 25 in FIG. 2 depicts a preferred alternative that uses a known process based upon average mutual information (AMI), represented by an AMI module 26 in FIG. 1, to determine the vector time delay. As known, average mutual information quantitates the information theoretic properties of chaotic systems. More specifically, average mutual information indicates how much information exists in the form of a time series, such as shown in Equation 1, about the measurement of that signal and shown in FIG. 1 concerning the measurement of that signal at a time Tdt later. That is, a time series v(n) for average mutual information indicates how much information will be available to predict the voltage level at a time Tdt later, i.e., the value v(n+T). Average mutual information processes distribute the measurements v(n) and v(n+T) over the set of measured data and determine the joint distribution of measurements of these two quantities. The first of these distributions is P(v(n)), the second is P(v(n+T), and the third is P(v(n),v(n+T)). The mutual information between these measurements is:

$$\ln\left[\frac{P(v(n), v(n+T))}{P(v(n))P(v(n+T))}\right] \quad (2)$$

where "ln" is the natural logarithm. For N observations, the average over all measurements is the AMI given by:

$$AMI = \sum_{n=1}^{N}\left[P(v(n), v(n+T))\ln\frac{P(v(n), v(n+T))}{P(v(n))P(v(n+T))}\right] \quad (3)$$

For independent measurements, each term in the above sum vanishes due to factorization of the joint probability P(a,b)=P(a)P(b). For the case T=0, I(0) is large because there is full knowledge of the measurements. Generally, however, I(T) will be greater than zero. The objective becomes determining an intermediate value of T that will preserve the information in the system without overburdening the process. With average mutual information, one approach is to choose the value for T that corresponds to the first minimum of I(T), although any value of T near the first minimum should suffice. As will be apparent the value of T can be any arbitrary number. Normally, the value will be refined so that it corresponds to an integer multiple of the sampling integral established in the converter 22.

Once the value T has been obtained, step 27 in FIG. 2 uses a time series vector representation generator 28 in the chaotic processor 14 to convert the digitized samples into a time series vector representation that has a sampling interval of T. Each vector points to the scalar value at an interval "T" later. More specifically the time series vector generator 28 in FIG. 1 operating in accordance with step 27 in FIG. 2 generates a d-dimensional set of vectors from a sequence of fixed vector time delays, T, in the form:

$$y(n)=v(n), v(n+T), v(n+2T), \ldots v(n+(d-1))T \quad (4)$$

where:

v(n) is the original time series datum at time index n;

v(n+T) is datum from the same time series offset in the positive direction by the vector time delay interval T;

v(n+2T) is datum from the same time series offset in the positive direction by the vector time delay interval 2T;

v(n+d−1)T is the datum offset by the vector delay interval (d−1)T where d is an embedding dimension to be obtained from an embedding delay value generator 30 in FIG. 1 as it processes step 31 in FIG. 2; and n is an index number for time series datum where n=1, 2, 3 . . . N and the maximum number of indices, N, may be selected to be any value.

The resulting time series vector is then analyzed to determine a minimum embedding function, "d". As with respect to the generation of the vector time delay interval, alternate approaches are available for determining the embedding delay value. A preferred approach that has produced reliable results utilizes a known "global false nearest neighbor" process that is implemented in the generator 30 by an GFNN module 32. Basically this process is based upon the concept that when points of higher dimension are projected down to a space of lower dimension, there are overlapping orbits in the low dimension space such that if the process were reversed and given space were projected to a higher dimension it could be reasonably expected that neighboring points along a trajectory would separate. Basically the process starts with a first dimension, unfolds the time series vector representation to higher and higher dimensions while keeping track of the percentage of nearest neighbors that spread apart at each integer increase of dimension. When the quality of the predictions or motions of neighbors become independent of the dimensions, the resulting delay for one representation to the other producing the desired result constitutes the minimum embedding value.

More specifically the process determines the dimension "d" with points made out of the vector representation in which the nearest neighbors ynn(n) of the point y(n) is given by:

$$ynn(n)=[vnn(n), vnn(n+T) \ldots vnn(n+(d-1)T)] \quad (5)$$

The process determines whether or not these points remain near in dimension (d+1), when vector y(n) is augmented by a component v(n+dT) and ynn(n) is augmented by vnn(n+dT). For small distances the neighbors are true neighbors. For large distances false neighbors exist. When the percentage of false neighbors drops to zero, the resulting delay is the minimum embedding dimension or delay value.

Figure 3:
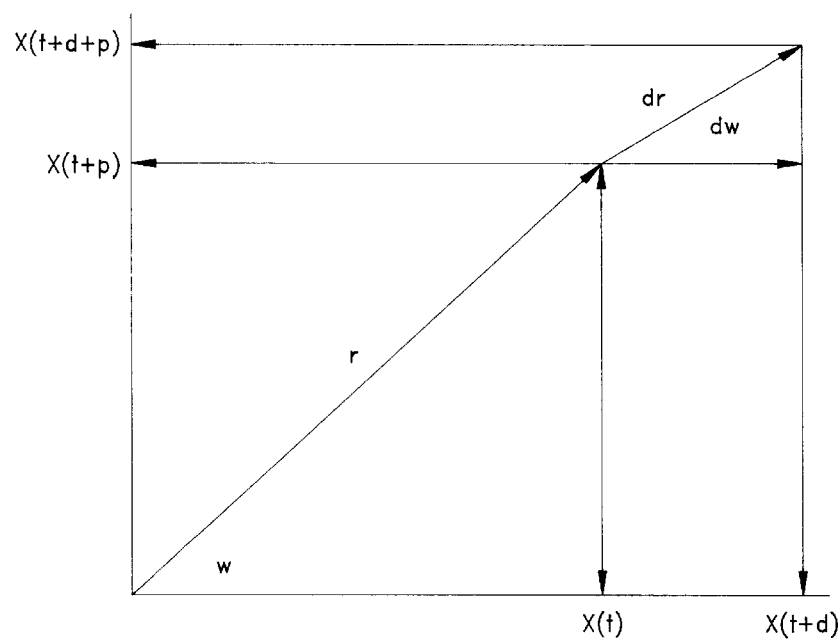
FIG. 3 is a diagram useful in understanding the operation of the apparatus and methods of FIGS. 1 and 2.

Once the minimum embedding delay value has been determined, step 33 in FIG. 2 and a chaotic radius processor 34 in FIG. 1 compare the magnitude of each term in the time series vector representation with a term delayed by the embedding delay value to obtain a chaotic radius for each term. More specifically, the chaotic radius processor 34 in FIG. 1 effectively plots the scalar value of each point in the vector series as shown in FIG. 3. On a horizontal scale and a vertical scale, X(t) and X(t+p) represent the component magnitudes of the vector at time "t", points X(t+d) and X(t+d+p) respectively represent the change in magnitude between two successive points at "t" and at (t+d). Consequently the chaotic radius (r) is given by:

$$r\sqrt{X(t)^2 + X(t+p)^2} \quad (6)$$

It will be further evident that the differential radius (dr) can be determined by:

$$dr = \sqrt{[[X(t+d) - X(t)]^2 + [X(t+d+p) - X(t+p)]^2} \quad (7)$$

or by $$dr=r(i+1)-r(i) \quad (8)$$

Step 35 in FIG. 2 and a differential radius processor 36 in FIG. 1 compute, for each vector in the time series vector representation, a corresponding differential radius, dr, according to either of the foregoing alternatives.

Referring again to FIG. 1, the chaotic radius or the differential radius can transfer from the chaotic radius processor 34 or differential radius processor 36 to a threshold detector 40 in the output 15. A threshold selector 41 can be adjusted for the signal corresponding to chaotic radius or differential chaotic radius for different cardio-respiratory functions in order to provide, on a display 42, a representation of the chaotic radius or differential chaotic radius.

With this understanding of the operation of the chaotic processor 14, reference is again made to the patient 12 in FIG. 1 undergoing diagnosis in accordance with this invention. The monitors 11 include, in addition to the oximeter 16, an ECG 44 that measures electrical heart activity; a heart rate monitor 45 measures heart rate; an air flow monitor 46 oral-nasal air flow; and a chest wall impedance monitor 47, chest wall effort. Each of the monitors 15 and 44 through 47 are well known in the art.

Figure 5:
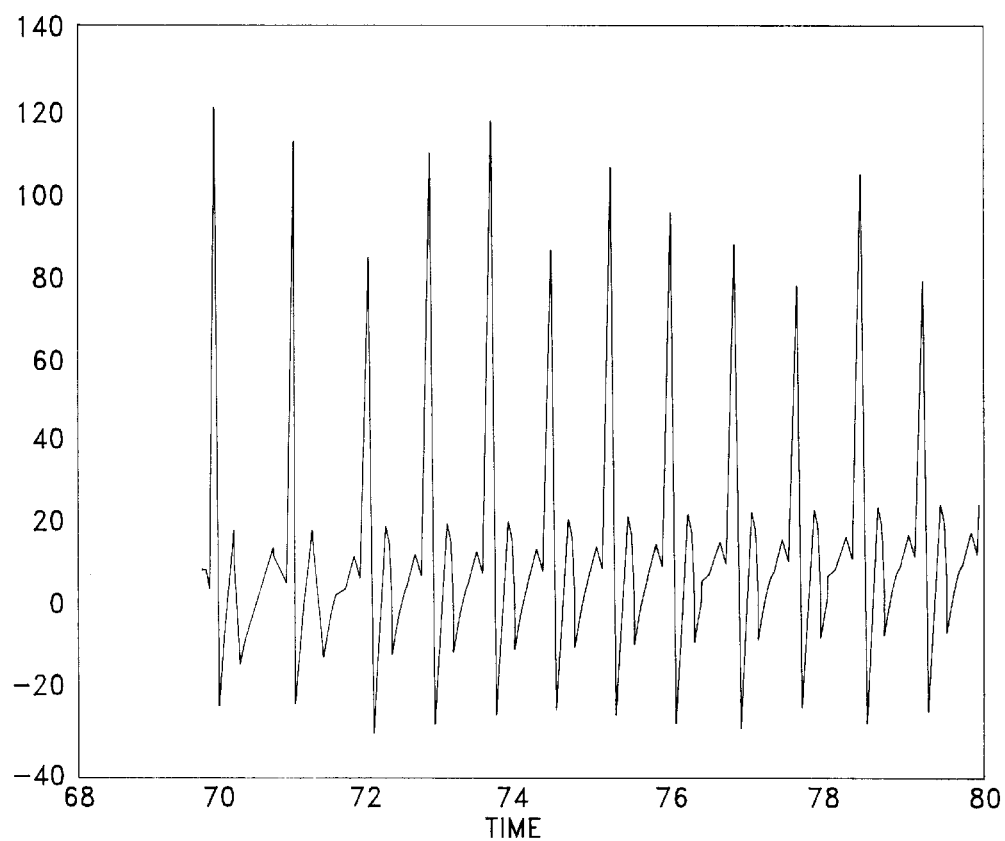
FIG. 5 is an enlarged view of the ECG trace in FIG. 4 during an event characteristic of a sleep breathing disorder.
Figure 4:
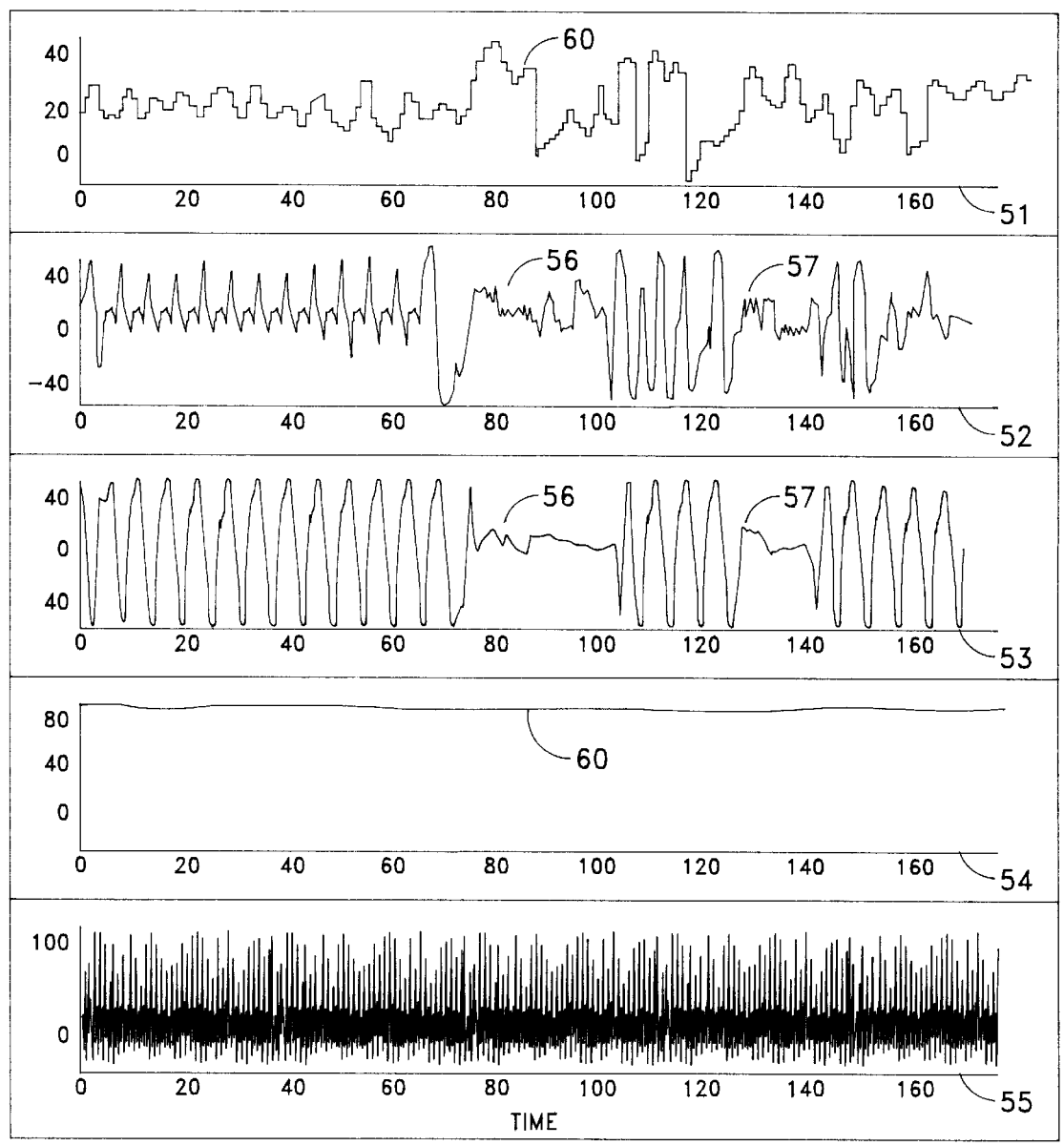
FIG. 4 discloses signals corresponding to several cardio-respiratory functions.

FIG. 4 depicts a multi-channel trace produced by a multi-channel chart recorder 50 including a heart rate traces produced by the heart rate monitor 45. The chest wall impedance monitor 47 produces a chest wall effort tracing 52; the air flow monitor 46, an air flow tracing 53; the oximeter 15, an oxygen saturation tracing 54; and the electrocardiograph 44, an ECG tracing 55. The chest tracing 52 and air flow tracing 53 indicate apnea events in separate intervals centered around 90 seconds and 130 seconds from the start of the record. There is a singular deflection on the oxygen saturation trace 54 shortly after 80 seconds at 60 and a variability in heart rate shown in the heart rate trace 51 irregularity in the heart at times following the point 60. There are no traces of an event of observation in the ECG trace 55. FIG. 5 depicts an enlarged version of the ECG trace during the interval spanning the event at 56. No definitive change is apparent.

Figure 6:
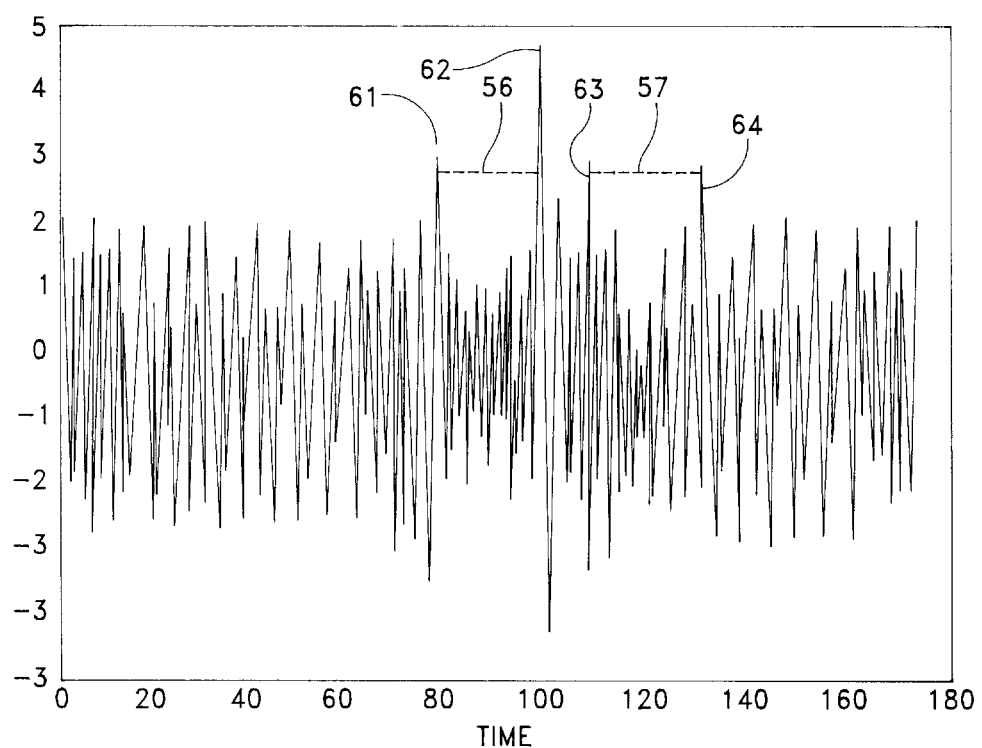
FIG. 6 depicts signals derived from the signals in FIG. 4.

FIG. 6 depicts the differential radius of the air flow measurements provided by the air flow monitor 46 as processed in the chaotic processor 13. Taking the normal maximums of the peaks of the differential radius as a threshold, it will be apparent that the differential radius produces markers that delineate the sleep apnea interval or dysfunction event namely by excursions 61 and 62 that bound the first event 56 and excursions 63 and 64 that bound the second event 57.

Figure 7:
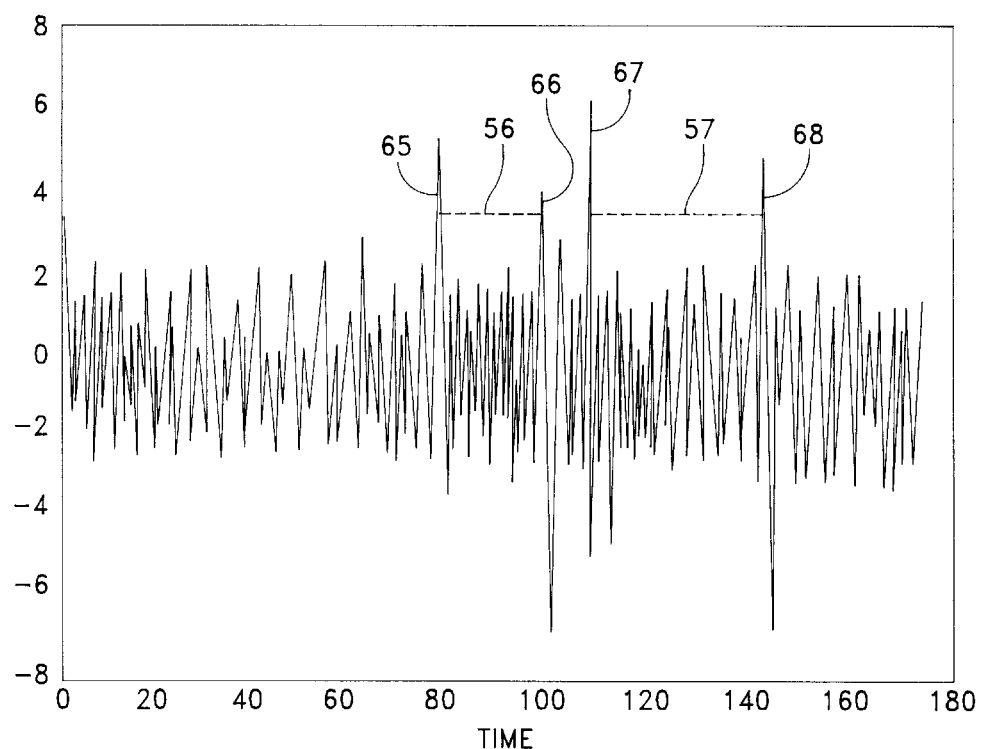
FIG. 7 depicts other signals derived from the signals in FIG. 4.

FIG. 7 depicts a similar analysis of the chest wall impedance signal from the chest wall impedance monitor 47. Again using a normal maximum as threshold, it is readily apparent that excursions 65 and 66 mark the event 56 while excursions 67 and 68 mark the event 57. Moreover, the timing of the marker excursions 65 through 68 correspond to the timing of the marker excursions 61 through 64 in FIG. 6.

Figure 8:
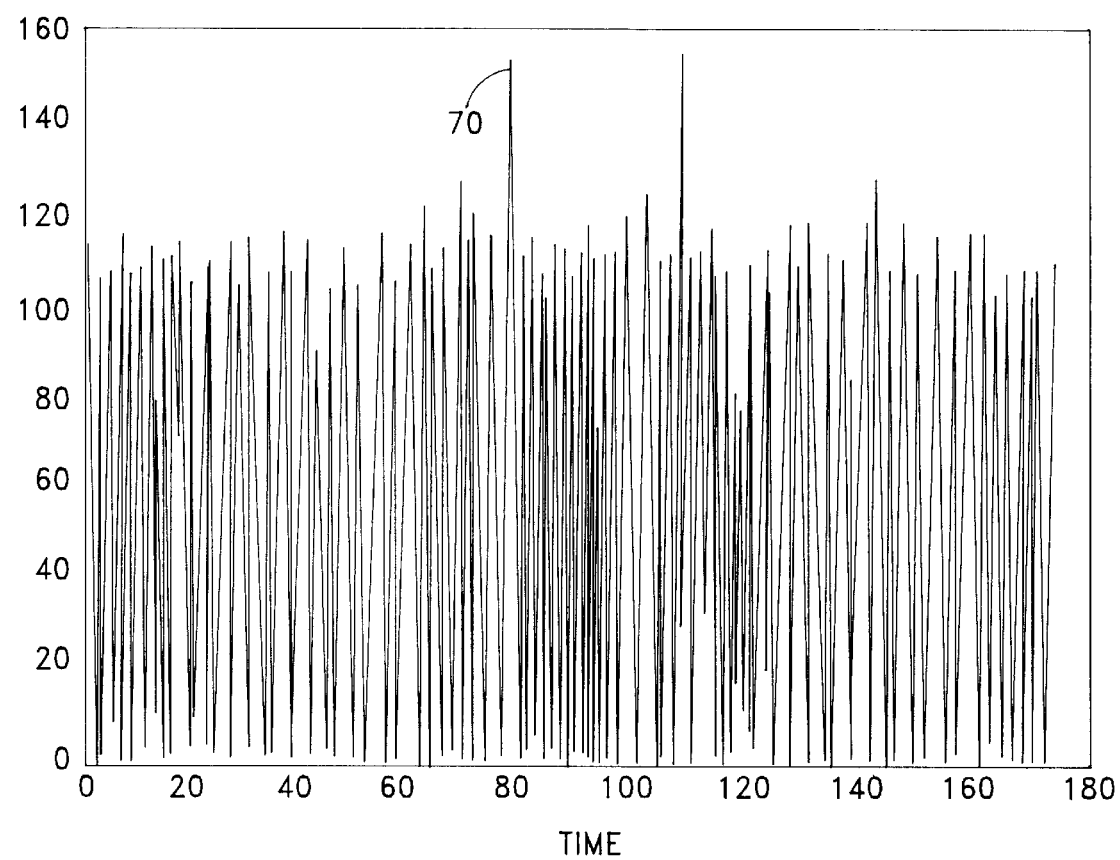
FIG. 8 depicts other signals derived from the signals in FIG. 4.

Similar analysis shows that chaotic processing of the heart rate trace in 51 and oxygen saturation trace 54 provide corresponding boundaries. Moreover, it has been found that the chaotic radius of the heart ECG signal as demonstrated in FIG. 8 at 70, is an optional marker ascertaining the onset of cardio-respiratory coupled dysfunction even though the ECG trace in FIG. 5 over the corresponding interval contains no such indication.

Consequently it will be apparent that the foregoing apparatus and method provide a diagnostic modality for obtaining a clear indication of the onset and duration of dysfunctional respiratory events. The time correlation of the events produced by the analyzing the different cardio-respiratory functions indicates that it may be possible to make a diagnosis without utilizing all five cardio-respiratory functions depicted in FIG. 4. A subset of one or more could be appropriate. It will also be apparent that even at high sampling frequencies, the data requirement for storing 16-bit samples for a single function over an eight-hour period is under 24 MBytes. Consequently the approach enables the recording of one or more cardio-respiratory functions over an extended sleep interval directly into digital form from which the vector time sample A/D converter 22 can produce a time series generator without any additional analog-to-digital conversion. Such a system would allow the recordings to be made in an in home situation, rather than a clinical setting, that is more conducive to a valid diagnosis.

As will also now be apparent, any number of available chaotic processing systems can be utilized to generate the information provided by the chaotic processor 14 shown in FIG. 1. The individual components in FIG. 1, particularly those in the processor 13 and threshold detector 40 may comprise discrete structures or software modules in a data processing system or a hybrid. The display 42 of the system in FIG. 1 can comprise a simple graphical display of the differential radius or radius over time or could superimpose either signal against a threshold. Alternatively a circuit for comparing the values of the differential chaotic radius or chaotic radius against the thresholds and automatically marking the time of such an excursion could also be produced in conjunction with the information contained in the chaotic processor 14.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed is:

1. A method for generating markers identifying the timing of the onset of an event characteristic of a sleep breathing disorder including the steps of:

monitoring at least one cardio-respiratory function over time;

generating a time series vector representation of each monitored cardio-respiratory function;

generating a signal for each monitored function based upon chaotic processing of the corresponding time series vector representation; and identifying as a marker each excursion of each signal beyond a corresponding threshold value thereby to indicate the timing of the onset of an event.

2. A method as recited in claim 1 wherein said monitoring includes monitoring first and second cardio-respiratory functions and said signal generating step includes generating a chaotic radius signal and a chaotic differential radius signal based upon chaotic and differential processing of the time series vector representations of the first and second cardio-respiratory functions, respectively.

3. A method as recited in claim 2 wherein the first monitored cardio-respiratory function is heart action as measured by an electrocardiograph and said monitoring, generating and identifying steps act on the signal from the electrocardiograph.

4. A method as recited in claim 2 wherein the second cardio-respiratory function is taken from the group of cardio-respiratory functions consisting of oral-nasal air flow, oxygen saturation, chest wall impedance and heart rate and said monitoring, generating and identifying steps act on at least one of each of the second functions.

5. A method as recited in claim 4 wherein the first monitored cardio-respiratory function is heart action as measured by an electrocardiograph and said monitoring, generating and identifying steps act on at least one of each of the first and second functions.

6. A method as recited in claim 2 wherein said generation of the differential radius signal includes:

generating an embedding delay value based upon the time series vector representation;

comparing the magnitudes of the terms of the vector representation at a given time and at a time delayed by the embedding delay value to obtain a chaotic radius; and generating in response to each value of the chaotic radius the differential chaotic radius for the given time.

7. A method as recited in claim 6 wherein said step of determining an embedding delay includes:

converting a monitored function into a time series of samples;

generating a vector time delay interval in response to the data in the time series of samples; and generating the time series vector representation based upon the value of the data in the time series of samples at intervals corresponding to the vector time delay interval.

8. A method as recited in claim 7 wherein said step of generating the vector time delay interval includes the step of obtaining average mutual information from the time series of samples.

9. A method as recited in claim 7 wherein said generation of the embedding delay value includes the step of obtaining global false nearest neighbor information from the time series vector representation.

10. A method as recited in claim 7 wherein said step of generating the differential chaotic radius includes comparing, at times corresponding to each vector time delay interval, the magnitude of the time series vector representation at that time and the magnitude of the time series vector representation at time offset by the embedding delay value.

11. A method as recited in claim 7 wherein:

the sampling frequency at which said time series representation is generated for each monitored function is greater than the greatest frequency of physiologic relevance with respect to the monitored cardio respiratory functions;

the vector time delay is an integer multiple of the sampling interval; and the embedding function is an integer multiple of the vector time delay.

12. A method as recited in claim 11 wherein the sampling frequency is at least 40 Hz.

13. Apparatus for generating markers identifying the timing of the onset of an event characteristic of a sleep breathing disorder including:

monitoring means for monitoring at least one cardio-respiratory function over time;

first means for generating a time series vector representation of each monitored cardio-respiratory function;

second means for generating a signal for each monitored function based upon chaotic processing of the corresponding time series vector representation; and marker identifying means for identifying as a marker each excursion of each signal from said second generating means beyond a corresponding threshold value thereby to indicate the timing of the onset of an event.

14. Apparatus as recited in claim 13 wherein said monitoring means includes means for monitoring first and second cardio-respiratory functions and said second generating means includes means for generating a chaotic radius signal and a chaotic differential radius signal based upon chaotic and differential processing of the time series vector representations of the first and second cardio-respiratory functions, respectively.

15. Apparatus as recited in claim 14 wherein said monitoring means includes an electrocardiograph for monitoring, as a first monitored cardio-respiratory function, heart action and said monitoring, first and second generating means and said marker identifying means act on the signal from the electrocardiograph.

16. Apparatus as recited in claim 14 wherein said monitoring means includes at least one of a group of cardio-respiratory function monitors consisting of thermistor means for monitoring oral-nasal air flow, finger pulse oximetry monitoring means for monitoring oxygen saturation, chest wall monitoring means for measuring chest wall impedance and heart rate monitoring means for monitoring heart rate and wherein first and second generating means and said marker identifying means act on signals from at least one of each of said group of monitoring means.

17. Apparatus as recited in claim 16 wherein said monitoring means includes an electrocardiograph for monitoring as a first monitored cardio-respiratory function heart action and said first and second generating means and said marker identifying means act on at least one of each of the first and second functions.

18. Apparatus as recited in claim 14 wherein said second generation means includes:

means for generating an embedding delay value based upon the time series vector representation;

means for comparing the magnitudes of the terms of the vector representation at a given time and at a time delayed by the embedding delay value to obtain a chaotic radius; and means for generating, in response to each value of the chaotic radius the differential chaotic radius for the given time.

19. Apparatus as recited in claim 18 wherein said embedding delay determining means includes:

means for converting a monitored function into a time series of samples;

means for generating a vector time delay interval in response to the data in the time series of samples; and means for generating the time series vector representation based upon the value of the data in the time series of samples at intervals corresponding to the vector time delay interval.

20. Apparatus as recited in claim 19 wherein said means for generating the vector time delay interval includes means for obtaining average mutual information from the time series of samples.

21. Apparatus as recited in claim 19 wherein said generation of the embedding delay value includes the step of obtaining global false nearest neighbor information from the time series vector representation.

22. Apparatus as recited in claim 19 wherein said means for generating the differential chaotic radius includes means for comparing, at times corresponding to each vector time delay interval, the magnitude of the time series vector representation at that time and the magnitude of the time series vector representation at time offset by the embedding delay value.

23. Apparatus as recited in claim 19 wherein said first generating means includes means for establishing a sampling frequency at which said time series representation is generated for each monitored function that is greater than the greatest frequency of physiologic relevance with respect to the monitored cardio respiratory functions and wherein the vector time delay is an integer multiple of the sampling interval and the embedding function is an integer multiple of the vector time delay.

24. Apparatus as recited in claim 19 wherein said first generating means includes means for establishing a sampling frequency of at least 40 Hz and wherein the vector time delay is an integer multiple of the sampling interval and the embedding function is an integer multiple of the vector time delay.

* * * * *